(12) United States Patent
Kang et al.

(10) Patent No.: US 7,795,302 B2
(45) Date of Patent: Sep. 14, 2010

(54) USE OF COMPOSITIONS FOR TREATING ROSACEA

(75) Inventors: Sewon Kang, Ann Arbor, MI (US); John J. Voorhees, Ann Arbor, MI (US); Gary J. Fisher, Ypsilanti, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1323 days.

(21) Appl. No.: 11/290,109

(22) Filed: Nov. 30, 2005

(65) Prior Publication Data

US 2006/0078582 A1    Apr. 13, 2006

Related U.S. Application Data

(62) Division of application No. 10/142,724, filed on May 9, 2002, now Pat. No. 7,078,048.

(60) Provisional application No. 60/289,758, filed on May 9, 2001.

(51) Int. Cl.
*A61K 31/35* (2006.01)
*A61K 31/19* (2006.01)
*A61K 31/12* (2006.01)
*A61K 31/497* (2006.01)

(52) U.S. Cl. ............... 514/460; 514/557; 514/558; 514/680; 514/252.1

(58) Field of Classification Search .......... 514/680, 514/557, 558, 460, 252.1
See application file for complete search history.

(56) References Cited

U.S. PATENT DOCUMENTS

| 5,679,374 | A | 10/1997 | Fanchon et al. |
|---|---|---|---|
| 5,879,688 | A | 3/1999 | Coury et al. |
| 5,895,649 | A | 4/1999 | De Lacharriere et al. |
| 5,932,215 | A * | 8/1999 | de Lacharriere et al. . 424/158.1 |
| 5,972,993 | A | 10/1999 | Ptchelintsev et al. |
| 6,001,885 | A | 12/1999 | Vega et al. |
| 6,110,924 | A | 8/2000 | Bosies et al. |
| 6,114,377 | A | 9/2000 | Schnittger et al. |
| 6,228,887 | B1 | 5/2001 | Kligman et al. |
| 6,284,802 | B1 | 9/2001 | Bissett et al. |
| 6,303,651 | B1 | 10/2001 | Hersh |
| 6,444,647 | B1 | 9/2002 | Robinson et al. |
| 6,517,847 | B2 | 2/2003 | Dow et al. |
| 6,664,287 | B2 * | 12/2003 | Avery et al. ............ 514/436 |
| 2002/0037914 | A1 | 3/2002 | Delong et al. |
| 2002/0182237 | A1 | 12/2002 | Bissett et al. |
| 2003/0130240 | A1 | 7/2003 | Ashley |
| 2003/0185839 | A1 | 10/2003 | Podolsky |
| 2005/0095261 | A1 | 5/2005 | Popp |

FOREIGN PATENT DOCUMENTS

| EP | 0 807 429 A1 | 11/1997 |
|---|---|---|
| WO | WO 97/39746 | 10/1997 |

OTHER PUBLICATIONS

European Search Report Dated Feb. 10, 2006 for Application No. 02744142.7-2123 PCT/US0214643.

* cited by examiner

*Primary Examiner*—Michael G Hartley
*Assistant Examiner*—Shirley V Gembeh
(74) *Attorney, Agent, or Firm*—Harness, Dickey & Pierce, P.L.C.

(57) ABSTRACT

Rosacea is treated with a composition comprising an antimicrobial and at least one of an anti-inflammatory and a non-retinoid inhibitor of at least one of NF-κB, AP-1, MMPs, adhesion molecules, TLRs, and CD14. The composition may further comprise a retinoid.

5 Claims, No Drawings

USE OF COMPOSITIONS FOR TREATING ROSACEA

RELATED APPLICATIONS

This application is a division of Ser. No. 10/142,724, filed 9 May 2002, now U.S. Pat. No. 7,078,048, which is based on provisional application 60/289,758, filed 9 May 2001, the disclosures of which are incorporated herein by reference.

BACKGROUND OF THE INVENTION

1. Field of the Invention

This invention describes methods and compositions for ameliorating the effects of rosacea, especially in combination with conventional therapy.

2. The State of the Art

Rosacea is a common facial dermatitis that currently affects an estimated 13 million Americans. It is a chronic and progressive cutaneous vascular disorder, primarily involving the malar and nasal areas of the face. Rosacea is characterized by flushing, erythema, papules, pustules, telanglectasia, facial edema, ocular lesions, and, in its most advanced and severe form, hyperplasia of tissue and sebaceous glands leading to rhinophyma. Rhinophyma, a florid overgrowth of the tip of the nose with hypervascularity and nodularity, is an unusual progression of rosacea of unknown cause. Ocular lesions are common, including mild conjunctivitis, burning, and grittiness. Blepharitis, the most common ocular manifestation, is a nonulcerative condition of the lid margins.

Rosacea most commonly occurs between the ages of 30 to 60, and may be seen in women experiencing hormonal changes associated with menopause. Women are more frequently affected than men; the most severe cases, however, are seen in men. Fair complexioned individuals of Northern European descent are most likely to be at risk for rosacea; most appear to be pre-disposed to flushing and blushing.

Alcohol, stress, spicy foods, and extremes of temperature have all been implicated, but none have been found to actually cause rosacea. One of the most famous rosacea sufferers was W. C. Fields; his on-screen association with alcohol likely fostered the unsubstantiated association between alcohol and rosacea. Although papules and pustules are associated with rosacea, and hence its misnomer as "acne rosacea", the occurrence of *P. acnes* is generally not associated with the condition.

The cause of rosacea is poorly understood, numerous theories have been offered. Hypotheses have included gastrointestinal, psychological, infectious, climatic, and immunological causes, although scientific evidence has not substantiated any of these as primary. Controlled studies have not demonstrated consistent preponderance of gastrointestinal symptoms in rosacea patients. Similarly, neither a distinct psychological abnormality nor one pharmacological mechanism has been isolated in rosacea patients. Perhaps the most commonly touted of the etiologic theories is based on the presence of *Demodex folliculorum* mites in patients with rosacea; the organism feeds on sebum, and in some cases treatment of *demodex* infestation has noted improvement in the rosacea; however, in a review of 79 biopsies in 1969, *demodex folliculorum* was noted in only 19% of the specimens. A bacterial cause for the disease has been hypothesized, but no consistent findings of one bacteria have been demonstrated. Climate, specifically exposure to extremes of sun and cold, may have an effect on the course of the disease, but the role of climate in what appears to be a connective tissue disorder is not clear. An autoimmune process has been suggested, and tissue fixed immunoglobulins have been reported in patients with chronic inflammation of rosacea, but no other evidence has been found. Other experimental evidence has suggested this disease may represent a type of hypersensitivity reaction. No single hypothesis appears to adequately explain both the vascular changes and the inflammatory reaction seen in rosacea, leaving the pathogenesis unclear. More recently, certain investigators have suggested a connection between rosacea and *H. pylori*, a bacteria shown to cause certain gastrointestinal ulcers, because symptoms seem to have abated in some ulcer patients also suffering rosacea. Nevertheless, the connection between *H. pylori* and rosacea has been questioned. H. Herr, *J Korean Med Sci* October 2000; 15(5):551-4; R. Boni, *Schweiz Med Wochenschr* 2000 Sep. 16; 130(37): 1305-8.

Histopathologic findings in rosacea dermatitis include vascular dilatation of the small vessels with perivascular infiltration of histiocytes, lymphocytes, and plasma cells. Dermal changes include loss of integrity of the superficial dermal connective tissue with edema, disruption of collagen fibers, and frequently severe elastosis. Follicular localization is infrequent and, when seen, is usually manifest clinically as pustules. However, there is no primary follicular abnormality. Rhinophyma is characterized histologically by an increase in sebaceous glands and connective tissue, follicular and vascular dilatation, edema, and a scattered infiltrate of perivascular lymphocytes and histiocytes. Immunoglobulin and compliment deposition at the dermal epidermal junction have been reported in conjunctival and skin biopsies from rosacea patients. Ocular pathologic findings include conjunctival and corneal infiltration with chronic inflammatory cells, including lymphocytes, epithelioid cells, plasma cells, and giant cells.

For the dermatological disease, the outcome of a successful management regimen is usually control rather than eradication of the disease. Advising the patient to avoid those stimuli that tend to exacerbate the disease—exposure to extremes of heat and cold, excessive sunlight, ingestion of hot liquids, alcohol, and spicy foods—may help. Although its mechanism of action is not clearly understood, the mainstay of treatment is the use of oral tetracycline, especially for the papular or pustular lesions. The dosage utilized is generally 250 mg every 6 hours for the first 3 to 4 weeks, followed by tapering based on clinical response. Doxycycline and minocycline (50-100 mg every 12 hours) are also effective and have the advantage of less frequent dosage and less concern over problems with gastrointestinal absorption. Patients who are intolerant to the tetracyclines may benefit from the use of erythromycin. Oral isotretinoin, in doses similar to those used for acne vulgaris, has also been effective for the inflammatory lesions, erythema, and rhinophyma. There is, however, no beneficial effect on the telangiectasias and isotretinoin may cause blepharitis and conjunctivitis. Other oral agents that have been used include ampicillin and metronidazole. Clonidine may also be of some value in reducing facial flushing. Topical therapy for rosacea is generally less successful than systemic treatment, although often tried first. Metronidazole (2-methyl-5-nitroimidazole-1-ethanol) may be effective topically; it is available commercially as a 0.75% gel and, when applied twice daily, substantially reduces inflammatory lesions; it is classified as an antiprotozoal. Although topical corticosteroids may effectively improve signs and symptoms, long-term therapy is not advisable since it may cause atrophy, chronic vasodilation, and telangiectasia formation. The treatment of chronic skin changes may require surgical intervention. Telangiectasias may be treated by electrocautery or using the tunable dye laser. Severerhinophyma is treated by paring with a scalpel, excision with skin grafting, dermabrasion, bipolar electrocautery, or by means of the argon or carbon dioxide laser.

The typical course of treatment is to start with metronidazole, and if that is not as effective as desired to ameliorate the symptoms, or the condition worsens, then therapy is switched to a stronger antimicrobial, such as tetracycline or minocycline. This standard course of therapy persists under the pretense that the antimicrobial is reducing inflammation, because inflammation appears to be reduced, even though it is logically the antimicrobial effects that cause the reduction in inflammation (and because these types of compounds are not known to have antiinflammatory properties).

In 1990, Akamatsu et al. ("The inhibition of free radical generation by human neutrophils through the synergistic effects of metronidazole with palmitoleic acid: a possible mechanism of action of metronidazole in rosacea and acne," Arch Dermatol Res 1990; 282(7):449-54) described the synergistic effects of metronidazole and palmitoleic acid on the anaerobic growth of *P. acnes* as well as on human neutrophil functions, including the generation of reactive oxygen species (ROS). Both metronidazole and palmitoleic acid, when used alone, only slightly inhibited the growth of *P. acnes*, and no significant decrease in human neutrophil functions, including the generation of ROS, was observed; but metronidazole used in the presence of palmitoleic acid (naturally present in human skin) markedly inhibited the anaerobic growth of *P. acnes* and decreased ROS generation by neutrophils. They conclude that by inhibiting oxidative tissue injury under in vivo conditions, treatment with metronidazole results in remarkable improvement of rosacea and acne.

U.S. Pat. No. 6,228,887 to Kligman discloses treating such skin disorders as photodamage, hyperpigmentation, rosacea, and scarring topically with high strength retinoids at a concentration effective to cause desquamation. Retinoids activate the the epidermal growth factor receptor, causing hyperproliferation of skin cells, which results in the desquamation sought by this patent. The clinical examples given in this patent only involve treating photodamaged skin.

SUMMARY AND OBJECTS OF THE INVENTION

The primary object of this invention is to supplement the treatment of rosacea by addressing the inflammatory and collagen-degrading components of the condition, through preferably topical administration of one or more compounds.

Thus, in one respect, this invention provides a method for treating rosacea that comprises administering to a patient in need thereof (i) an antimicrobial and (ii) at least one of (a) an anti-inflammatory and (b) a non-retinoid inhibitor of at least one AP-1, NF-κB, MMP, and TLR. In a preferred embodiment, the composition also includes a retinoid, which typically acts to inhibit AP-1, NF-κB, and various MMPs, although some retinoids may inhibit fewer than all of these. Most preferably, the anti-inflammatory and/or the non-retinoid inhibitor is administered topically.

In another respect, this invention provides a topical composition for treating rosacea which comprises a combination of an antimicrobial and at least one of (a) an anti-inflammatory and (b) a non-retinoid inhibitor of at least one AP-1, NF-κB, MMP, and TLR.

DETAILED DESCRIPTION OF PREFERRED EMBODIMENTS

While likely distinct, the present invention may be better understood with respect to the present inventors' findings in the treatment of acne. Acne is a multifactorial disease, developing in the sebaceous follicles. At least one agent thought responsible is the anaerobe *Propionibacterium acnes* (*P. acnes*); in younger individuals, practically no *P. acnes* is found in the follicles of those without acne. In general, there are four major principles presently governing the therapy of acne: (i) correction of the altered pattern of follicular keratinization; (ii) decrease sebaceous gland activity; (iii) decrease the follicular bacterial population (especially *P. acnes*) and inhibit the production of extracellular inflammatory products through the inhibition of these microorganisms; and (iv) produce an anti-inflammatory effect. The present treatments for acne following these principals typically include: vitamin A acid (retinoic acid), known for its comedolytic properties, administered topically (e.g., Retin-A® brand 0.025% all-trans retinoic acid cream) or systemically (e.g., Accutane® brand 13-cis retinoic acid); an antibiotic administered systemically (e.g., tetracycline or one of its derivatives) or topically (e.g., benzoyl peroxide, erythromycin, clindamycin, azelaic acid); the use of other comedolytic agents such as salicylic acid; or the use of systemic anti-androgens such as cyproterone acetate and spironolactone (because androgens promote sebum production, and sebum has been found to be comedogenic and inflammatory), which may be administered in combination with an estrogen.

The art has addressed inflammation and scarring caused by acne as a secondary benefit to the treatment of the disease; that is, if the acne is cured the factors causing scarring will be eliminated. There is otherwise no treatment directed at preventing scarring from acne. Neither is there presently any direct treatment for the inflammation accompanying acne. The conventional treatment acts to prevent further problems by alleviating the cause of the acne; for example, a patient is treated with tetracycline, an antibiotic, in hopes of killing the *P. acnes*, and the death of the bacteria will effectively end the inflammation and future scarring. Much as antipyretics, analgesics, decongestants, and antihistamines have been developed to treat the symptoms of colds and upper respiratory infections (as opposed to antibiotics and antivirals to kill off the invading bacteria and viruses), there is a need for treatments diminishing if not preventing scarring and inflammation in acne.

In connection with acne, we have discovered that neutrophils (PMNs), immune cells that migrate to areas of injury, invade acne-affected skin, and release both a collagenase (MMP-8) and another protease (neutrophil elastase) that likely exacerbate scarring. Additionally, we have discovered that acne-affected skin has an elevated collagenase (MMP-1) level from resident skin cells that further exacerbates scarring. We have disclosed that inhibition of these dermal matrix-degrading enzymes with the use of MMP inhibitors (in addition to and including retinoids) can lessen scarring of acne-affected skin. Neutrophils circulate in the blood and therfore must be recruited by a signalling mechanism to induce their presence in the skin, facilitate their infiltration to the affected site, and enable their release of MMP-8 and elastase. Accordingly, impeding or disrupting the signalling which induces their presence in the skin and/or the activity of MMP-8 or elastase is likely to diminish the accompanying inflammation and the degradatory action of MMP-8 and/or elastase.

Although rosacea is not believed to be cause by *P. acnes*, the conventional wisdom is that rosacea is caused or exacerbated by demodex mites which live in human hair follicles. The present inventors believe that these microbes cause an inflammatory reaction, analogous to the inflammation described in connection with inflammation in acne. It is believed that the inflammatory agent is excretia from the mites, a protein shed by the mite, a CD-14 binding protein carried by the mite that activates a TLR (toll-like receptor), or some combination thereof, and the inflammatory reaction is believed to involve AP-1, NF-κB, and the subsequent production of MMPs in the skin.

Accordingly, a treatment that inhibits TLR activation of NF-κB and/or that inhibits induction of polymorphonuclear lukocytes would likely aid in the treatment of rosacea. Activation of the TLRs causes NF-κB to enter the cell nucleus of keratinocyes. The keratinocytes are thus induced to release chemotactic factors, especially cytokines (IL-1β, IL-8, IL-10, TNFα). These factors activate the AP-1 and NF-κB pathways, and NF-κB activates more IL-1 and TNFα (a cyclical process, such as in FIG. 1 of U.S. Pat. No. 5,837,224 on photoaging due to UV radiation). The release of these factors causes inflammation, including the recruitment of neutrophils (PMNs; i.e., polymorphonuclear leukocytes) from the blood supply to the area from which the signallying was sent; MMP-8 and elastase are preformed in the neutrophils and so when the neutrophils arrive at the site of the rosacea, these dermal matrix-degrading enzymes arrive at the area. The cytokines also effect other keratinocytes and fibroblasts (FB), which are resident in the skin, to generate MMPs.

CD-14 is a "pattern recognition" protein that is a part of the innate immune response in humans. It binds to LPS-like substances, such as are produced by *P. acnes*. When the bound CD-14 encounters a toll-like receptor (TLR), it binds to it and thereby activates it. It is believed (without being constrained thereto) that a compound (likely a protein) produced, excreted, or otherwise shed by *demodex* likely binds to CD14 proteins. These bound proteins then activate TLRs, which causes or exacerbates the inflammation in rosacea. Alternatively, the *demodex* may have on its surface compounds that bind to CD14, such that the bound complex breaks off from the mite, or the mite otherwise transfers the complex to the TLR, which causes the inflammatory reaction.

This inflammatory response can directly induce MMPs. The NF-κB from the TLR causes cells to produce inflammatory cytokines, such as TNFα, IL-1β, IL-8, and/or IL-10. TNFα and IL-1β, acting through NF-κB, can induce keratinocytes and fibroblasts to produce MMPs. On the other front, IL-8 and IL-10 induce chemotaxis and adhesion molecules to recruite PMNs from the blood stream; these cells have their own supply of MMP-8 and elastase, and so bring these matrix degrading enzymes to the site of inflammation, namely rosacea. This mechanism would appear to be facilitated by the hypervascularity associated with rosacea, providing a well-infused site and thus hyper-recruitement of PMNs because of the increased vascularity at the affected site.

It might seem counter-intuitive that MMP induction could result in hyperplasia leading to rhinophyma. In this regard, fibroblasts are sensitive to the matrix around them: when in contact with an intact matrix, they tend to be less active and to produce little collagen; when in the presence of gelatin (collagen breakdown products), then tend to produce more collagen to repair the matrix. There may likely be a cycle whereby some factor (such as bacteria or the *demodex* mites) causes inflammation that induces MMPs, and the collage breakdown products induces collagen production and hyperplasia; as the cause of inflammation persists and so the breakdown products are constantly being formed, the fibroblasts are prompted to proliferate and produce more collagen, and those newly proliferated fibroblasts will also be prompted to proliferate and produce more collagen.

Accordingly, it is likely important to break this cycle at multiple points. Thus, in combination with existing antimicrobial or isotretinoin therapy, this invention adds an anti-inflammatory therapy. The present therapy includes as an adjunct to oral isotretinoin therapy or antimicrobial therapy an inhibitor of NF-κB, AP-1, and/or of MMPs. Alternatively, as an adjunct to antimicrobial therapy, this invention provides the use of a topical retinoid, which inhibits NF-κB and AP-1 induction of MMPs, as well as inhibiting JNK induction of MMPs.

Aspirin and E5510 (described by Fujimori, T., et at., Jpn J Pharmacol (1991) 55(I):81-91) inhibit NF-κB activation. Farnesyl transferase inhibitors such as B-581 (described by Garcia A. M., et al., J Biol Chem (1993) 268(25):18415-18), BZA-5B (described by Dalton M. B. et al., Cancer Res (1995) 55(15):3295-3304), farnesyl acetate, and (α-hydroxyfarnesyl) phosphoric acid act on RAS and thus inhibit activation of the resultant ERK cascade; ERK leads to c-fos, which heterodimerizes with c-jun to create AP-1. Other useful inhibitors are those that inhibit NF-κB, such as sulfasalazine and parthenolide, serine protease (elastase) inhibitors, and anti-adhesion molecules such as neutrophil infiltration inhibitors (e.g., selectin antagonists).

As used herein, "inhibitors" of MMPs and other dermal matrix-degrading enzymes, such as elastase, inhibit one or more of the steps in the natural physiological pathways leading to the production of these enzymes and/or directly inhibit one or more of these proteases, or they directly inhibit the activity of the enzyme. Thus, as used herein an "inhibitor" excludes retinoids, inasmuch as retinoids and tetracyclines have been known for treating acne, this invention is directed to the novel use of a non-retinoid enzyme inhibitor, which use may be combined with the conventional use of a retinoid and/or a tetracycline. Thus, an "inhibitor" is a non-retinoid compound that directly inhibits one or more dermal matrix-degrading enzymes and/or indirectly inhibits the enzyme by inhibiting some portion of an upstream pathway(s) leading to one or more of these dermal matrix-degrading enzymes. Inhibition of the upstream pathway of these dermal matrix-degrading enzymes includes inhibition of one or more of the various signalling compounds and/or of the transcription factors (e.g., NF-κB, or cJUN and cFOS which together create AP-1) by which these enzymes are produced naturally.

MMPs are also inhibited by BB2284 (described by Gearing, A. J. H. et al., *Nature* (1994) 370:555-557), GI129471 (described by McGeehan G. M., et al., *Nature* (1994) 370: 558-561), and TIMPs (tissue inhibitors of metalloproteinases, which inhibit vertebrate collagenases and other metalloproteases, including gelatinase and stromelysin). Other compounds useful for the present invention are direct MMP inhibitors such as hydroxamate and hydroxy-urea derivatives, the latter exemplified by Galardin, Batimastat, and Marimastat, and those disclosed in EP-A1-0 558635 and EP-A1-0 558648 (disclosed as useful for inhibiting MMPs in the treatment of, among other etiologies, skin ulcers, skin cancer, and epidermolysis bullosa).

Indirect MMP inhibitors include the kinase inhibitors genistein and quercetin (as described in U.S. Pat. Nos. 5,637, 703, 5,665,367, and FR-A-2,671,724, and related compounds, as well as other antioxidants such as NAC (N-acetyl cysteine), discussed below. Still further, other kinase inhibitors such as SB202190 (described by Lee, J. C., et al., Nature (1994) 372:739-746) and PD98059 (described by Dudley, D. T., et al., PNAS (USA) (1995) 92:7686-7689) inhibit specific kinases in the cascades, geranyl geranyltransferase inhibitors and lisofylline, which inhibit activation of the JNK cascade resulting from RAC/CDC42 activation, and U0126 (1,4-diamino-2,3-dicyano-1,4-bis[2-aminophenylthio]butadiene).

As noted above, compounds that inhibit cytokines are indirect

MMP inhibitors because interrupting the signalling pathway effectively inhibits MMPs. MMPs are also inhibited by BB2284 (described by Gearing, A. J. H. et al., Nature (1994) 370:555-557), GI129471 (described by McGeehan G. M., et al., Nature (1994) 370:558-561), and TIMPs (tissue inhibitors of metalloproteinases, which inhibit vertebrate collagenases and other metalloproteases, including gelatinase and stromelysin). Still other compounds useful for the present invention include hydroxamate and hydroxy-urea derivatives which are direct MMP inhibitors, and which are exemplified by such compounds as Galardin, Batimastat, and Marimastat, and those disclosed in EP-A1-0 558635 and EP-A1-0 558648 (as useful for inhibiting MMPs in the treatment of, among other etiologies, skin ulcers, skin cancer, and epidermolysis bullosa).

Inhibitors of activator protein-1 (AP-1) are likely to inhibit the subsequent signalling that results in the presence of MMPs in the dermal matrix; the more of the pathway that is inhibited, the more likely there will be no induction of MMPs. Among various compounds that have been found to inhibit AP-1 and may likely be used topically include the following. Cannabinoids: Faubert and Kaminski; "AP-1 activity is negatively regulated by cannabinol through inhibition of its protein components, c-fos and c-jun", *J Leukoc Biol*, vol. 67, no. 2 (February 2000, pp. 259-66) (Cannabinoid compounds exhibit immunosuppressive actions that are putatively mediated through Gi-protein coupled receptors that negatively regulate adenylate cyclase. However, recent studies suggest that cannabinoids modulate other signaling cascades. Cannabinol inhibited binding to AP-1-containing sites from the interleukin-2 promoter, in part, due to decreased nuclear expression of c-fos and c-jun. Thus, cannabinoid-induced immunosuppression involves disruption of the ERK signaling cascade.) Deferroxamine (DFO); Kramer-Stickland et al., "Inhibitory effects of deferoxamine on UVB-induced AP-1 transactivation", *Carcinogenesis*, vol. 20, no. 11, November 1999, pp. 2137-42 (Production of reactive oxygen species (ROS) by iron can contribute directly to DNA and protein damage and may contribute to cell signaling and proliferation. DFO treatment 24 h prior to UVB irradiation reduced UVB-induced AP-1 transactivation by approximately 80%, with the effect of DFO diminishing as pre-treatment time was shortened. Treatment with $FeCl(3)$ a minimum of 6 h prior to UVB potentiated the UVB induction of AP-1 transactivation by 2-3-fold.) Separately, gadolinium chloride and alpha-tocopherol: Camandola et al., "Liver AP-1 activation due to carbon tetrachloride is potentiated by 1,2-dibromoethane but is inhibited by alpha-tocopherol or gadolinium chloride", *Free Radic Biol Med*, vol. 26, no. 9-10, May 1999, pp. 1108-16. Cyclosporin A: Sugano et al., "Cyclosporin A inhibits collagenase gene expression via AP-1 and JNK suppression in human gingival fibroblasts, *J Periodontal Res*, vol. 33, no. 8, November 1998, pp. 448-452 (Cyclosporin A is able to affect signal transduction of lipidpolysaccharide-induced collagenase expression in fibroblasts; treatment of fibroblasts with LPS caused activation of collagenase gene, activator protein-1 (AP-1) and c-Jun N-terminal kinase (JNK). These activations were blocked by CsA. They suggest that inhibitory effects of CsA on LPS-induced signal transduction may contribute to the mechanism of CsA-induced gingival overgrowth. Catachins: Barthelman et al., "(−)-Epigallocatechin-3-gallate inhibition of ultraviolet B-induced AP-1 activity", *Carcinogenesis*, vol. 19, no. 12, December 1998, pp. 2201-4 (using cultured human keratinocytes, UVB-induced AP-1 activity is inhibited by EGCG in a dose range of 5.45 nM to 54.5 microM; EGCG is effective at inhibiting AP-1 activity when applied before, after or both before and after UVB irradiation; EGCG also inhibits AP-1 activity in the epidermis of a transgenic mouse model). Naphthopyranomycins and exfoliamycins, such as K1115 A (Naruse et al., "K115A, , a new anthraquinone that inhibits the binding of activator protein-1 (AP-1) to its recognition sites II. Taxonomy, fermentation, isolation, physico-chemical properties and structure determination," *J Antibiot* (Tokyo), vol 51, no. 6, June 1998, pp. 545-52; the anthraquinone 3,8-dihydroxy-1-propylanthraquinone-2-carboxylic acid). DHEA: Dashtaki et al., "Dehydroepiandrosterone and analogs inhibit DNA binding of AP-1 and airway smooth muscle proliferation", *J Pharmacol Exp Ther*, vol. 285, no. 2, 1998 May (pp. 876-83) (dehydroepiandrosterone (DHEA) and its analogs such as 16-alpha-bromoepiandrosterone). Oleanolic acid glycosides: Lee et al., "Momordins inhibit both AP-1 function and cell proliferation," *Anticancer Res*, vol. 18, no. 1A, January-February 1999 (pp. 119-24). Monoterpene perillyl alcohol: Barthelman et al., "Inhibitory effects of perillyl alcohol on UVB-induced murine skin cancer and AP-1 transactivation", *Cancer Res.*, vol. 58, no. 4, 15 Feb. 1998 (pp. 711-6). Curcumin, which inhibits both AP-1 and NF-κB: Xu et al., "Curcumin inhibits IL1 alpha and TNF-alpha induction of AP-1 and NF-kB DNA-binding activity in bone marrow stromal cells," *Hematopathol Mol Hematol*, vol. 11, no. 1, 1997-8 (pp. 49-62); and Pendurthi et al., "Suppression of activation of transcription factors Egr-1, AP-1, and NF-kappa B," *Arterioscler Thromb Vasc Biol*, vol. 17, no. 12, December 1997 (pp. 3406-13); and Bierhaus et al., "The dietary pigment curcumin reduces endothelial tissue factor gene expression by inhibiting binding of AP-1 to the DNA and activation of NF-kappa B," *Thromb Haemost*, vol. 77, no. 4, 1997 April (pp. 772-82). Aspirin (acetylsalicylic acid): Huang et al., "Inhibition of ultraviolet B-induced activator protein-1 (AP-1) activity by aspirin in AP-1-luciferase transgenic mice", *J Biol Chem*, vol. 272, no. 42, 17 Oct. 1997 (pp. 26325-31). Pyrrolidine dithiocarbamate and N-acetyl cysteine (inhibit AP-1, NF-κB, and IL-8): Munoz et al., "Pyrrolidine dithiocarbamate inhibits the production of interleukin-6, interleukin-8, and granulocyte-macrophage colony-stimulating factor by human endothelial cells in response to inflammatory mediators: modulation of NF-kappa B and AP-1 transcription factors activity", *Blood*, vol. 88, no. 9, 1996 Nov. 1 (pp. 3482-90). Metal salts, such as gold (I) and selenite: Handel et al., "Inhibition of AP-1 binding and transcription by gold and selenium involving conserved cysteine residues in Jun and Fos," *Proc Natl Acad Sci USA*, vol. 92, no. 10, 1995 May 9 (pp. 4497-501) (in electrophoretic mobility-shift analyses, AP-1 DNA binding was inhibited by gold(I) thiolates and selenite, with 50% inhibition occurring at approximately 5 microM and 1 microM, respectively; and other metal ions inhibited at higher concentrations, in a rank order correlating with their thiol binding affinities); and Spyrou et al, "AP-1 DNA-binding activity is inhibited by selenite and selenodiglutathione", *FEBS Lett*, vol. 368, no. 1, 1995 Jul. 10 (pp. 59-63) (selenite and selenodiglutathione (GS-Se-SG)); and Williams et al., "Aurothioglucose inhibits induced NF-kB and AP-1 activity by acting as an IL-1 functional antagonist", *Biochim Biophys Acta*, vol. 1180, no. 1, 1992 Oct. 13 (pp. 9-14).

NF-κB inhibitors include those disclosed in the following references. Cyclopentenone prostaglandins: Rossi et al., "Anti-inflammatory cyclopentenone prostaglandins are direct inhibitors of IkappaB kinase", *Nature*, vol. 403, no. 6765, 2000 Jan. 6 (pp. 103-8). Quercetin and staurosporine: Peet and Li, "IkappaB kinases alpha and beta show a random sequential kinetic mechanism and are inhibited by staurosporine and quercetin", *J Biol Chem*, vol. 274, no. 46, 1999 Nov. 12 (pp. 32655-61) (but not the quercetin analogue Daidzein).

Nepalolide A: Wang et al., "Nepalolide A inhibits the expression of inducible nitric oxide synthase by modulating the degradation of IkappaB-alpha and IkappaB-beta in C6 glioma cells and rat primary astrocytes", *Br J Pharmacol*, vol. 128, no. 2, 1999 September (pp. 345-56). Turmeric (curcumin): Plummer et al., "Inhibition of cyclo-oxygenase 2 expression in colon cells by the chemopreventive agent curcumin involves inhibition of NF-kappaB activation via the NIK/IKK signalling complex", *Oncogene*, vol. 18, no. 44, 1999 Oct. 28 (pp. 6013-20). Salicylates: Stevenson et al., "Salicylic acid and aspirin inhibit the activity of RSK2 kinase and repress RSK2-dependent transcription of cyclic AMP response element binding protein- and NF-kappa B-responsive genes", *J Immunol*, vol. 163, no. 10, 1999 Nov. 15 (pp. 5608-16). Diterpenes: de las Heras et al., "Inhibition of NOS-2 expression in macrophages through the inactivation of NF-kappaB by andalusol", *Br J Pharmacol*, vol. 128, no. 3, 1999 October (pp. 605-12) (andalusol, ent-6α,8α, 18-trihydroxy-13(16),14-labdadiene, is a naturally occurring diterpene, isolated from Sideritis foetens (Lamiaceae). N-substituted benzamides: Liberg et al., "N-substituted benzamides inhibit NFkappaB activation and induce apoptosis by separate mechanisms", *Br J Cancer*, vol. 81, no. 6, 1999 November (pp. 981-8). While not preferred due to potential toxicity issues, arsenic: Estrov et al., "Phenylarsine oxide blocks interleukin-1β-induced activation of the nuclear transcription factor NF-κB, inhibits proliferation, and induces apoptosis of acute myelogenous leukemia cells", *Blood*, vol. 94, no. 8, 1999 Oct. 15 (pp. 2844-53). Genistein: Tabary et al., "Genistein inhibits constitutive and inducible NFkappaB activation and decreases IL-8 production by human cystic fibrosis bronchial gland cells", *Am J Pathol*, vol. 155, no. 2, 1999 August (pp. 473-81). Theophylline: Tomita et al., "Functional assay of NF-kappaB translocation into nuclei by laser scanning cytometry: inhibitory effect by dexamethasone or theophylline", *Naunyn Schmiedebergs Arch Pharmacol*, vol. 359, no. 4, 1999 April (pp. 249-55). Cepharanthine: a plant alkaloid (I) (Merck Index 11, 306, 1981), and described in U.S. Pat. Nos. 2,206,407 and 2,248,241, and Japanese Patents 120,483, 128,533, and 141,292. Trifluoroalkyl salicylates: Bayon et al., "4-trifluoromethyl derivatives of salicylate, triflusal and its main metabolite 2-hydroxy-4-trifluoromethylbenzoic acid, are potent inhibitors of nuclear factor kappaB activation", *Br J Pharmacol*, vol. 126, no. 6, 1999 March (pp. 1359-66) (2-hydroxy-4-trifluoromethylbenzoic acid (HTB) and 2-acetoxy-4-trifluoromethylbenzoic acid (triflusal), both more potent than aspirin or salicylate as inhibitors of NF-κB, indicating that the incorporation of a 4-trifluoromethyl group to the salicylate molecule strongly enhances its inhibitory effect on NF-κB activation). Quinapril: quinapril hydrochloride is chemically described as [3S-[2[R*(R*)],3R*]]-2-[2-[[1-(ethoxycarbonyl)-3-phenyl-propyl]amino]-1-oxopropyl]-1,2,3,4-tetrahydro-3-isoquinolinecarboxylic acid, monohydrochloride. Its empirical formula is $C_{25}H_{30}N_2O_5 \cdot HCl$. Cyclosporine A: Meyer et al, "Cyclosporine A is an uncompetitive inhibitor of proteasome activity and prevents NF-kappaB activation", *FEBS Lett*, vol. 413, no. 2, 1997 Aug. 18 (pp. 354-8). Arachidonic acid derivatives: Thommensen et al., "Selective inhibitors of cytosolic or secretory phospholipase A2 block TNF-induced activation of transcription factor nuclear factor-kappa B and expression of ICAM-1", *J Immunol*, vol. 161, no. 7, 1998 Oct. 1 (pp. 3421-30) (TNF-induced activation of NF-κB inhibited by trifluoromethyl ketone analogue of arachidonic acid ($AACOCF_3$), methyl arachidonyl fluorophosphate, trifluoromethyl ketone analogue of eicosapentaenoic acid ($EPACOCF_3$), 12-epi-scalaradial, and LY311727; arachidonyl methyl ketone analogue ($AACOCH_3$) and the eicosapentanoyl analogue ($EPACHOHCF_3$) had no effect on TNF-induced NF-κB activation. Genistein, erbstatin: Natarajan et al., "Protein tyrosine kinase inhibitors block tumor necrosis factor-induced activation of nuclear factor-κB, degradation of IκBα, nuclear translocation of p65, and subsequent gene expression", *Arch Biochem Biophys*, vol. 352, no. 1, 1998 Apr. 1 (pp. 59-70). Fasudil: 1-(5-isoquinolinesulfonyl)homopiperazine hydrochloride (fasudil hydrochloride); Sato et al., "Inhibition of human immunodeficiency virus type 1 replication by a bioavailable serine/threonine kinase inhibitor, fasudil hydrochloride", *AIDS Res Hum Retroviruses*, vol. 14, no. 4, 1998 Mar. 1 (pp. 293-8). ACE (angiotensin converting enzyme) inhibitors, like quinipril: Hernandez-Presa et al., "Angiotensin-converting enzyme inhibition prevents arterial nuclear factor-kappa B activation, monocyte chemoattractant protein-1 expression, and macrophage infiltration in a rabbit model of early accelerated atherosclerosis", *Circulation*, vol. 95, no. 6, 1997 Mar. 18 (pp. 1532-41). Synthetic 1,3,7-trialkyl xanthine derivatives, such as pentoxifylline (3,7-dimethyl-1-(5-oxohexyl) xanthine; Drugs & Aging 1995, 7/6: 480-503) and denbufylline (1,3-dibutyl-7-(2-oxopropyl)xanthine); Lee et al., "Pentoxifylline blocks hepatic stellate cell activation independently of phosphodiesterase inhibitory activity", *Am J Physiol*, vol. 273, no. 5 Pt 1, 1997 November (pp. G1094-100). Benzophenanthradine derivatives: Chaturvedi et al., "Sanguinarine (pseudochelerythrine) is a potent inhibitor of NF-κB activation, IκBα phosphorylation, and degradation", *J Biol Chem*, vol. 272, no. 48, 1997 Nov. 28 (pp. 30129-34) (sanguinarine, a benzophenanthridine alkaloid). Actinomycin D: Faggioli et al., "Protein synthesis inhibitors cycloheximide and anisomycin induce interleukin-6 gene expression and activate transcription factor NF-κB", *Biochem Biophys Res Commun*, vol. 233, no. 2, 17 Apr. 1997 (pp. 507-13) (IL-6 mRNA accumulation in two human cell lines, MDA-MB-231 and HeLa, stimulated by cycloheximide or anisomycin is almost completely inhibited in the presence of actinomycin D). Hydroxyanthranilic acids: Sekkai et al., "Inhibition of nitric oxide synthase expression and activity in macrophages by 3-hydroxyanthranilic acid, a tryptophan metabolite", *Arch Biochem Biophys*, vol. 340, no. 1, 1997 Apr. 1 (pp. 117-23) (3-hydroxyanthranilic acid but not anthranilic acid). Nordihydroguaiaretic acid and AA861: Lee et al., "Inhibition of 5-lipoxygenase blocks IL-1 beta-induced vascular adhesion molecule-1 gene expression in human endothelial cells", *J Immunol*, vol. 158, no. 7, 1997 Apr. 1 (pp. 3401-7). Prostaglandin A1: Rossi et al., "Inhibition of nuclear factor kappa B by prostaglandin A1: an effect associated with heat shock transcription factor activation", *Proc Natl Acad Sci USA*, vol. 94, no. 2, 1997 Jan. 21 (pp. 746-50).

Sialyl Lewis X (SLe.sup.x) mediates binding of neutrophils to vascular endothelial cells by binding to E-selectin. (M. Phillips, et al., *Science* 1990, 250, 1130.; J. Lowe, et al., *Cell* 1990, 63, 475; T. Feizi, *Trends Biochem Sci* 1991, 16, 84; M. Tiemeyer., et al., *Proc. Natl. Acad. Sci. USA* 1991, 88, 1138; L. Lasky, *Science* 1992, 258, 964; and T. Springer, L. A. Lasky, *Nature* 1991, 349, 196.) Sialyl Lewis X (SLe.sup.x) is a cell surface carbohydrate ligand found on neutrophils, anchored onto the outer membrane thereof by integral membrane glycoproteins and/or glycolipids. Administration of SLe.sup.x inhibits the SLe.sup.x/E-selectin interaction and blocks adhesion of neutophils to endothelial cells. (M. Buerke, et al., *J. Clin. Invest.*, 1994, 1140.). Neutrophil-mediated inflammatory diseases may be treated by administration of Sialyl Lewis X (SLe.sup.x). Selectin inhibitor include those in the following references. E-, P-, and L-selectin inhibitors in U.S. Pat. No. 5,830,871. Sulfatides and sialylated or sulfated fucooligosaccharides, as described in U.S. Pat. No. 5,985,852, and other fucose derivatives as described in U.S. Pat. Nos. 5,962,422 and 5,919,769; as well as described by Ikami et al., "Synthetic studies on selectin ligands-inhibitors: Synthesis and inhibitory activity of 2-O-fucosyl sulfatides containing 2-branched fatty alkyl residues in place of ceramide", *Journal of Carbohydrate Chemistry*, vol. 17, no. 3, 1998 (pp. 453-470) (sulfated 2-O-alpha-L-fucopyranosyl beta-D-galactopyranosides containing 2-branched fatty-alkyl residues in place of ceramide); Todderud et al., "BMS-190394, a selectin inhibitor, prevents rat cutaneous inflammatory reactions", *J Pharmacol Exp Ther*, vol. 282, no. 3, 1997 September (pp. 1298-304) (selectin antagonist BMS-190394, a structural analog of sulfatide). TBC-1269 (available from Texas Biotechnology Corp., Houston, Tex.) and other mannose derivatives: for example, Dupre et al., "Glycomimetic selectin inhibitors: (alpha-D-mannopyranosyloxy)methylbiphenyls", *Bioorganic & Medicinal Chemistry Letters*, vol. 6, no. 5, 1996 (pp. 569-572); Lin et al., "Synthesis of sialyl Lewis x mimetics as selectin inhibitors by enzymatic aldol condensation reactions", *Bioorg Med Chem*, vol. 7, no. 3, 1999 March (pp. 425-33) (D-mannosyl phosphate/phosphonate derivatives enzymatically prepared as sialyl Lewis x tetrasaccharide mimics); Kogan et al., "Rational design and synthesis of small molecule, non-oligosaccharide selectin inhibitors: (alpha-D-mannopyranosyloxy)biphenyl-substituted carboxylic acids", *J Med Chem*, vol. 38, no. 26, 1995 Dec. 22 (pp. 4976-84). Leumedins: Endemann et al., "Novel anti-inflammatory compounds induce shedding of L-selectin and block primary capture of neutrophils under flow conditions", *J Immunol* 15 May 1997; 158(10):4879-85 (leumedins are small molecules that inhibit neutrophil movement into inflamed tissues). Di- and tri-valent small molecules, mainly 3-carboxyaralkyl-substituted 2-α-D-mannopyranosyloxy-phenyl unsubstitued, oxygen-, or nitrogen-substituted alkanes (e.g., oxobutane, piperidine), as described in U.S. Pat. No. 5,919,768. GSC-150: Wada et al., "Effect of GSC-150, a new synthetic selectin inhibitor, on skin inflammation in mice", *Japanese Journal of Pharmacology*, vol. 71, no. Suppl. 1, 1996 (Page 302P). Sialyl Lewis x analogs: Kiso et al., "Studies of selectin binding inhibitors: Synthesis of sialyl-Lewis x and sialyl-Lewis a epitope analogs containing 2-acetamido derivative of N-methyl-1-deoxynojirimycin", *Journal of Carbohydrate Chemistry*, vol. 15, no. 1, 1996 (pp. 1-14) (synthesis of sialyl-Lewis x (15) and sialyl-Lewis a (17) epitope analogs containing the 2-acetamido derivative of N-methyl-1-deoxynojirimycin ). Glycolipid sulfatide: Nair et al., "Inhibition of immune complex-induced inflammation by a small molecular weight selectin antagonist", *Mediators of Inflammation*, vol. 3, no. 6, 1994 (pp. 459-463). Triterpene glucosides such as glycyrrhizin: Rao et al., "Glycyrrhetinic acid glycosides are sialyl Lewis X mimics, and function as selectin inhibitors", *Molecular Biology of the Cell*, vol. 5, no. Suppl., 1994 (pp. 480A); Narasinga et al., "Sialyl Lewis X Mimics Derived from a Pharmacophore Search Are Selectin Inhibitors with Anti-inflammatory Activity", *Journal of Biological Chemistry*, vol. 269, no. 31, 1994 (pp. 19663-19666) (glycyrrhizin, an L-fucose derivative, and a C-fucoside derivative; Subramanian et al., "Attenuation of renal ischemia-reperfusion injury with selectin inhibition in a rabbit model", *Am J Surg*, vol. 178, no. 6, December 1999 (pp. 573-6). GM-1925: Cornell and Bowyer, "Attenuation of lung injury in a rabbit acid aspiration model using GM-1925, a novel selectin inhibitor", *Surgical Forum*, vol. 45, 1994 (pp. 107-110). Diisopropyl fluorophosphate: Palecanda et al., "Complete inhibition of cross-linking and activation induced shedding of I selectin by the serine protease inhibitor diisopropyl fluorophosphate DPF", *J Immunol*, vol. 150, no. 8 Part 2, 1993 (page 304A). BR 44-09 and BR 44-096837: Heavner et al., "Multiple binding site involvement in neutrophil selectin adhesion implications for design of peptide and carbohydrate inhibitors BIO BR 44-09 BR 44-096840", *J Cell Biochem Suppl*, no. 17 Part A, 1993 (p. 342); Dalton et al., Inhibition of selectin mediated adhesion in-vivo and in-vitro BIO BR 44-09 BR 44-096837", *J Cell Biochem Suppl*, no. 17 Part A, 1993 (p. 342). GMP-140: May et al., "GMP-140 P Selectin inhibits human neutrophil activation by lipopolysaccharide analysis by proton magnetic resonance spectroscopy BIO BA 93-00 BA 93-130631", *Biochem Biophys Res Commun*, vol. 183, no. 3, 1992 (pp. 1062-1069). Tetrasaccharides: Ushakova et al., "Inhibitory activity of monomeric and polymeric selectin ligands", *Vopr Med Khim*, vol. 45, no. 5, 1999 September-October (pp. 375-83) (tetrasaccharides SiaLex, SiaLea, HSO$_3$Lex, their conjugates with polyacrylamide (40 kDa), and several other monomeric and polymeric substances; all monomeric inhibitors were about two orders of magnitude weaker; PAA-conjugates, containing as a ligand tyrosine-o-sulfate in addition to one of the above mentioned oligosaccharides, were the most potent synthetic blockers compared with fucoidan, bi-ligand glycoconjugate HSO3Lea-PAA-sTyr); Bertozzi et al., "Sulfated disaccharide inhibitors of L-selectin: deriving structural leads from a physiological selectin ligand", *Biochemistry*, vol. 34, no. 44, 1995 Nov. 7 (pp. 14271-8) (generated a simple small molecule (lactose 6',6-disulfate) with greater inhibitory potency for L-selectin than sialyl Lewis x). Panosialins: Shinoda et al., "Panosialins, inhibitors of an alpha1,3-fucosyltransferase Fuc-TVII, suppress the expression of selectin ligands on U937 cells", *Glycoconj J*, vol. 15, no. 11, November 1998 (pp. 1079-83). CY-1503: Schmid et al., "Carbohydrate selectin inhibitor CY-1503 reduces neutrophil migration and reperfusion injury in canine pulmonary allografts", *J Heart Lung Transplant*, vol. 16, no. 10, 1997 October (pp. 1054-61). Inhibitors of TLRs (toll-like receptors) and/or other receptors that are sensitive to the LPS-like compounds associated with acne lesions can be used to ameliorate the signalling that induces the cytokines TNFα, IL-1β, IL-8, and IL-10, as shown in FIGS. 6 and 8B, and any other related cytokines that are induced by the *P. acnes* bacteria. Diglucosamine-based LPS antagonists include E5564 and E5531, described by E. Lien et al., *J. Biol. Chem.* 276(3): 1873-80 (2001), and by T. K. Means et al., *J. Immunol.*, 166(6): 4074-82 (2001), inhibit certain TLRs.

Antimicrobials are those commonly used, including those described or discussed above. Other antimicrobials can include doxycycline and minocycline and other tetracycline derivatives. Patients who are intolerant to the tetracyclines may benefit from the use of erythromycins such as Erythrocin, Ery-C, E-Mycin; azithromycins such as Zithromax; or clarithromycins such as Biaxin, as well as possibly milbemycins and related compounds. Other possible antibiotics include aminoglycosides such as amikacin, gentamicin, kanamycin, neomycin, netilmicin, paromomycin, streptomycin, or tobramycin; penicillins such as penicillin V or amoxicillin; the combination of a penicillin with beta-lactamase inhibitors, which protect the penicillin from bacterial enzymes that may destroy it before it can do its work, an example of such a combination would be Augmentin; cephalosporins and examples of these include cefaclor (Ceclor), cefadroxil (Duricef), cefazolin (Ancef, Kefzol, Zolicef), cefixime, (Suprax), cefoxitin (Mefoxin), cefprozil (Cefzil), ceftazidime (Ceptaz, Fortaz, Tazicef, Tazideme), cefuroxime (Ceftin) and cephalexin (Keflex); fluoroquinolones and examples of these include ciprofloxacin (Cipro), trovafloxacin (Trovan), levofloxacin (Levaquin), norfloxacin (Noroxin), and ofloxacin (Floxin); streptogramins, and sulfonamides including sulfisoxazole (Gantrisin) and the combination drug sulfamethoxazole and trimethoprim (Bactrim, Cotrim).

Generally, molecules having a molecular weight of less than about 600 will pass through the skin, and lipophilic molecules are preferred (or a conjugate having a lipophilic portion). Accordingly, while short chain peptides are not listed above, those having a low molecular weight and a high proportion of lipophilic amino acid residues are likely to be useful as topical inhibitors of AP-1, NF-κB, elastase, and/or selectin.

The compositions of this invention can be provided in any cosmetically suitable form, preferably as a lotion or cream, but also in an ointment or oil base, as well as a sprayable liquid form (e.g., a spray that includes the MMP inhibitor in a base, vehicle, or carrier that dries in a cosmetically acceptable way without the greasy appearance that a lotion or ointment would have if applied to the skin).

In addition, the compositions contemplated by this invention can include one or more compatible cosmetically acceptable adjuvants commonly used, such as colorants, fragrances, emollients, humectants, and the like, as well as botanicals such as aloe, chamolile, and the like.

When used topically, an inhibitor (of a dermal matrix-degrading enzyme) is used preferably at concentrations of between about 0.05% and about 5%, more preferably between 0.1% and 1%.

One enzyme that degrades retinoids and can be inhibited is cytochrome P-450. In the skin, retinoids are converted into retinoic acid (RA) as the active form. Natural retinoids that function in the skin are all trans or are metabolized to all trans Retinoic acid (RA; all trans) is metabolized to inactivation by hydroxylation (via RA 4-hydroxylase) to 4-hydroxy-RA, which is then oxidized by a reaction mediated by the cytochrome P-450-dependent monooxygenase system. (S. Kang et al., "Liarozole Inhibits Human Epidermal Retinoic Acid 4-Hydroxylase Activity and Differentially Augments Human Skin Responses to Retinoic Acid and Retinol In Vivo," *J. Invest. Dermatol.*, 107:183-187 (August 1996); E. A. Duell et al., "Human Skin Levels of Retinoic Acid and Cytochrome P-450-derived 4-Hydroxyretinoic Acid after Topical Application of Retinoic Acid In Vivo Compared to Concentrations Required to Stimulate Retinoic Acid Receptor-mediated Transcription In Vitro," *J. Clin. Invest., Skin Retinoid Levels and Reporter Gene Activity*, 90:1269-1274 (October 1992); E. A. Deull et al., "Retinoic Acid Isomers Applied to Human Skin in Vivo Each Induce a 4-Hydroxylase That Inactivates Only Trans Retinoic Acid," *J. Invest. Dermatol.*, 106:316-320 (February 1996). Accordingly, compounds which interfere with the elimination metabolism of all trans RA, the active metabolite of topically applied retinoids such as 9-cis RA and 13-cis RA, will beneficially increase the amount of RA in the skin. Thus, preventing the degradation of natural (all trans) RA in the skin effectively increases its concentration, and so provides the benefits useful for its treatment of acne.

Retinoids that are likely to be useful for treating rosacea include natural and synthetic analogs of vitamin A (retinol), vitamin A aldehyde (retinal), vitamin A acid (retinoic acid (RA)), including all-trans, 9-cis, and 13-cis retinoic acid), etretinate, and others as described in EP-A2-0 379367, U.S. Pat. Nos. 4,887,805, and 4,888,342 (the disclosures of which are incorporated herein by reference), and the dissociating retinoids that are specific for AP-1 antagonism (such as those described by Fanjul, et al. in Nature (1994) 372:104-110). Various synthetic retinoids and compounds having retinoid activity are expected to be useful in this invention, to the extent that they exhibit anti-MMP activity in vivo, and such are described in various patents assigned on their face to Allergan Inc., such as in the following U.S. Pat. Nos. 5,514,825; 5,698,700; 5,696,162; 5,688,957; 5,677,451; 5,677,323; 5,677,320; 5,675,033; 5,675,024; 5,672,710; 5,688,175; 5,663,367; 5,663,357; 5,663,347; 5,648,514; 5,648,503; 5,618,943; 5,618,931; 5,618,836; 5,605,915; 5,602,130. Still other compounds described as having retinoid activity are described in other U.S. Pat. Nos. 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,343,173; 5,426,118; 5,414,007; 5,407,937; 5,399,586; 5,399,561; 5,391,753, and the like.

Examples of compounds dermatologically acceptable and having or likely to have inhibitory effects on the CYP-26 (P-450) mediated degradation of RA and other retinoids include azoles, especially triazoles, including, for example, ketoconazole (U.S. Pat. Nos. 4,144,346 and 4,223,036), fluconazole (U.S. Pat. No. 4,404,216), itraconazole (U.S. Pat. No. 4,267,179), liarozole, irtemazole, and the like; compounds related to these that may also be useful include, for example, diazines such as flucytosine.

It would also be beneficial to use such cytochrome P-450 inhibitors in combination with a reduced amount of retinoid; the P-450 inhibitor decreases the metabolic elimination of the retinoid and so less retinoid is needed to achieve the same result. Still further, analytical methods are available for determining whether a given compound inhibits the degradation of RA by applying the compound and testing for changes in CRABP (cytoplasmic retinoic acid binding protein), which will have increased levels if the levels of RA are also increased by the topical application of the test compound.

It would also be useful to use inhibitors of CD-14, a pattern recognition protein, part of the innate immune response of humans, that binds to LPS-like substances and activates TLRs.

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A method of treating rosacea comprising administering at least one of an antimicrobial and a retinoid, in combination with an inhibitor of Toll-like receptors (TLRs) selected from the group consisting of: E5564 and E5531, wherein the inhibitor is topically administered to a site of rosacea.

2. The method of claim 1, wherein the antimicrobial is selected from the group consisting of: tetracycline or a derivative thereof, erythromycin or a derivative thereof, azithromycin, clarithromycin, milbemycin, aminoglycoside, penicillin optionally in combination with a beta-lactamase inhibitor, cephalosporin, fluoroquinolone, streptogramin, sulfonamide, and compatible mixtures thereof.

3. The method of claim 1, wherein the antimicrobial, the retinoid, or the antimicrobial and the retinoid are orally administered.

4. The method of claim 1, wherein the antimicrobial is topically administered to the site of rosacea.

5. The method of claim 1, further comprising administering a cytochrome P-450 inhibitor selected from the group consisting of: ketoconazole, fluconazole, itraconazole, liarozaole, irtemazole, flucytosine, and compatible mixtures thereof.

* * * * *

UNITED STATES PATENT AND TRADEMARK OFFICE
CERTIFICATE OF CORRECTION

PATENT NO. : 7,795,302 B2
APPLICATION NO. : 11/290109
DATED : September 14, 2010
INVENTOR(S) : Sewon Kang, John J. Voorhees and Gary J. Fisher It is certified that error appears in the above-identified patent and that said Letters Patent is hereby corrected as shown below:

Column 4, line 54, "therfore" should be --therefore--.

Column 4, line 62, "cause" should be --caused--.

Column 5, line 11, "keratinocyes" should be --keratinocytes--.

Column 5, line 19, "signallying" should be --signaling--.

Column 5, line 59, "collage" should be --collagen--.

Column 6, line 9, "et at." should be --et al.--.

Column 8, line 48, "gold(1)" should be --gold(I)--.

Column 8, line 57, "Biochim" should be --Biochem--.

Column 9, line 55, ".HC1" should be --•HCl--.

Signed and Sealed this
Twenty-second Day of February, 2011

David J. Kappos
*Director of the United States Patent and Trademark Office*